(12) United States Patent
Head et al.

(10) Patent No.: US 9,333,189 B2
(45) Date of Patent: May 10, 2016

(54) TAXANE- AND TAXOID-PROTEIN COMPOSITIONS

(75) Inventors: Jonathan F. Head, Baton Rouge, LA (US); Robert L. Elliott, Baton Rouge, LA (US)

(73) Assignee: ONCBIOMUNE, INC., Baton Rouge, LA (US)

(*) Notice: Subject to any disclaimer, the term of this patent is extended or adjusted under 35 U.S.C. 154(b) by 803 days.

(21) Appl. No.: 13/017,173

(22) Filed: Jan. 31, 2011

(65) Prior Publication Data

US 2011/0190204 A1 Aug. 4, 2011

Related U.S. Application Data

(60) Provisional application No. 61/301,006, filed on Feb. 3, 2010.

(51) Int. Cl.

| A61K 47/48 | (2006.01) |
|---|---|
| A61K 38/40 | (2006.01) |
| A61K 31/337 | (2006.01) |
| A61K 9/00 | (2006.01) |
| A61K 38/18 | (2006.01) |
| A61K 38/22 | (2006.01) |
| A61K 38/38 | (2006.01) |
| A61K 45/06 | (2006.01) |
| A61K 47/42 | (2006.01) |
| A61K 47/44 | (2006.01) |

(52) U.S. Cl.
CPC .......... *A61K 31/337* (2013.01); *A61K 9/0019* (2013.01); *A61K 38/1808* (2013.01); *A61K 38/2257* (2013.01); *A61K 38/38* (2013.01); *A61K 38/40* (2013.01); *A61K 45/06* (2013.01); *A61K 47/42* (2013.01); *A61K 47/44* (2013.01); *A61K 47/483* (2013.01); *A61K 47/48284* (2013.01)

(58) Field of Classification Search
CPC ..................................................... A61K 47/48
USPC ........................................ 514/19.3, 1.1, 15.3
See application file for complete search history.

(56) References Cited

U.S. PATENT DOCUMENTS

| 5,043,101 | A | * | 8/1991 | Gordon ...................... 252/408.1 |
| 5,362,478 | A | | 11/1994 | Desai et al. |
| 5,439,686 | A | | 8/1995 | Desai et al. |
| 5,498,421 | A | | 3/1996 | Grinstaff et al. |
| 5,665,382 | A | | 9/1997 | Grinstaff et al. |
| 5,916,596 | A | | 6/1999 | Desai et al. |
| 6,096,331 | A | | 8/2000 | Desai et al. |
| 6,310,039 | B1 | * | 10/2001 | Kratz ........................... 514/19.5 |
| 6,506,405 | B1 | | 1/2003 | Desai et al. |
| 6,537,579 | B1 | | 3/2003 | Desai et al. |
| 6,749,868 | B1 | | 6/2004 | Desai et al. |
| 6,753,006 | B1 | | 6/2004 | Desai et al. |
| 6,825,166 | B2 | | 11/2004 | McChesney et al. |
| 7,285,646 | B2 | | 10/2007 | Bauer |
| 7,414,073 | B2 | | 8/2008 | Baloglu et al. |
| 7,417,023 | B2 | | 8/2008 | Faulk |
| 2003/0185793 | A1 | * | 10/2003 | Kratz ............................ 424/85.1 |
| 2004/0220086 | A1 | | 11/2004 | Faulk |
| 2006/0246005 | A1 | | 11/2006 | Yang et al. |
| 2006/0275308 | A1 | * | 12/2006 | Warrell et al. .............. 424/155.1 |
| 2007/0232536 | A1 | | 10/2007 | Hegedus |
| 2008/0160095 | A1 | | 7/2008 | Desai |
| 2008/0226549 | A1 | | 9/2008 | Sirbasku |
| 2009/0068104 | A1 | | 3/2009 | Faulk |
| 2009/0099336 | A1 | | 4/2009 | Payne et al. |
| 2009/0181048 | A1 | | 7/2009 | Kamei et al. |
| 2009/0196933 | A1 | | 8/2009 | De |
| 2009/0208591 | A1 | | 8/2009 | Bernstein |

OTHER PUBLICATIONS

NCBI—MeSH-transferrin.*
Patent Cooperation Treaty, Notification Concerning Transmittal of International Preliminary Report on Patentability, in international application No. PCT/US11/023112, dated Aug. 16, 2012 (10 pages).
Baloglu et al., The Taxane Diterpenoids. J. Nat. Prod. 1999, 62, 1448-1472.
Cazzola et al., Manipulations of cellular iron metabolism for modulating normal and malignant cell proliferation: achievements and prospects. Blood, vol. 75, No. 10 May 15, 1990: pp. 1903-1919.
Reizenstein, Iron, Free Radicals and Cancer. Med. Oncol. Tumor Pharmacother. 1991; 8(4):229-33.
Saul et al., A dual-ligand approach for enhancing targeting selectivity of therapeutic nanocarriers. Journal of Controlled Release 114 (2006) 277-287.
Kreitman, Immunotoxins for Targeted Cancer Therapy. The AAPS Journal 2006; 8(3):E532-51.
Lim et al., Transferrin-Oligomers as Potential Carriers in Anticancer Drug Delivery. Pharmaceutical Research, vol. 21, No. 11, (2004) 1985-1992.
Lai et al., Effects of artemisinin-tagged holotransferrin on cancer cells. Life Sciences 76 (2005) 1267-1279.
Johnson et al., The Role of the Diphtheria Toxin Receptor in Cytosol Translocation. J Biol. Chem. 1988; 263(3): 1295-300.
Hu-Lieskovan et al., Sequence-Specific Knockdown of EWS-FLI1 by Targeted, Nonviral Delivery of Small Interfering RNA Inhibits Tumor Growth in a Murine Model of Metastatic Ewing's Sarcoma. Cancer Res. 2005; 65(19): 8984-92.
Tros et al., Antitumoral activity of transferrin-lipoplexes carrying the IL-12 gene in the treatment of colon cancer. Journal of Drug Targeting, Sep. 2006; 14(8): 527-535.

(Continued)

*Primary Examiner* — Yan Xiao
(74) *Attorney, Agent, or Firm* — McAndrews Held & Malloy, Ltd.

(57) ABSTRACT

Compositions comprising a taxane or taxoid, such as paclitaxel, and a protein, such as albumin or a metal-transferrin, such as gallium-transferrin, can be prepared by combining an aqueous protein solution with a second solution containing the taxane or taxoid, a non-ionic surfactant, and an alcohol; adjusting the pH of the combined solutions to between about 7.9 and about 8.3; and purifying the pH-adjusted solution to remove solutes having a molecular weight less than 10,000 Da. Such compositions can be prepared that are substantially free of non-ionic surfactants, such as Cremophor EL, and are useful in the treatment of cancers, such as breast cancer.

8 Claims, 3 Drawing Sheets

(56) References Cited

OTHER PUBLICATIONS

Maruyama et al., Intracellular targeting of sodium mercaptoundecahydrododecaborate (BSH) to solid tumors by transferrin-PEG liposomes, for boron neutron-capture therapy (BNCT). Journal of Controlled Release 98 (2004) 195-207.

Chin et al., Efficient delivery of a Bcl-2-specific antisense oligodeoxyribonucleotide (G3139) via transferrin receptor-targeted liposomes. Journal of Controlled Release 112 (2006) 199-207.

Green et al, Abraxane, a novel Cremophor-free, albumin-bound particle form of paclitaxel for the treatment of advanced non-small-cell lung cancer. Annals of Oncology 17: 1263-1268, 2006.

Gomme, P.T. et al., "Transferrin: structure, function and potential therapeutic actions", Drug Discovery Today, Elsevier, Rahway, NJ, US., vol. 10, No. 4, Feb. 15, 2005, pp. 267-273, XP004741337, ISSN: 1359-6446, D0I: 10.1016/S1359-6446(04)03333-1, p. 271, left-hand column, line 40-right-hand column, line 38.

\* cited by examiner

TAXANE- AND TAXOID-PROTEIN COMPOSITIONS

CROSS-REFERENCE TO RELATED APPLICATIONS

This application claims the priority of the filing date of U.S. Provisional Application Ser. No. 61/301,006, filed Feb. 3, 2010, which is hereby incorporated by reference in its entirety.

FIELD OF THE INVENTION

This invention relates to compositions comprising taxanes or taxoids and proteins, such as albumin or transferrin, useful for the treatment of cancers.

BACKGROUND OF THE INVENTION

Taxanes are a family of compounds that includes paclitaxel, a cytotoxic natural product, and docetaxel, a semi-synthetic derivative, two compounds that are widely used in the treatment of cancer, E. Baloglu and D. G. I. Kingston, J. Nat. Prod. 62: 1448-1472 (1999). Taxanes are mitotic spindle poisons that inhibit the depolymerization of tubulin, resulting in cell death. While docetaxel and paclitaxel are useful agents in the treatment of cancer; their antitumor activity is limited because of their non-specific toxicity towards normal cells. These off target associations can cause complications ranging from inflammation to the death of the patient.

Due to the particular insolubility of taxanes, pharmaceutical forms have been difficult to formulate. For example, TAXOL® (Bristol-Myers Squibb) utilizes a formulation containing paclitaxel dissolved in Cremophor® EL (a polyethoxylated castor oil) and ethanol, as a delivery agent. However, Cremophor® EL has been called a dose limiting agent because of its toxicities. In particular, the Cremophor® EL vehicle can have serious side effects including severe hypersensitivity reactions. ABRAXANE® (Abraxis BioScience, LLC) utilizes a human blood albumin-bound nanoparticulate form of paclitaxel, thereby eliminating Cremophor® EL. However, while such nanoparticles may bond to and internalize to tumor cells via gp60 endothelial cell surface receptors, they are not specifically targeted to tumor cells.

A common approach to target therapeutics specifically to cancer cells is to conjugate anti-cancer agents to antibodies or functional fragments. However, antibody therapy may result in significant levels of non-specific cellular association. The serum iron transport protein transferrin (Tf) has been investigated as a potential drug carrier. Conjugation of anticancer agents to Tf allows for specific targeting to cancer cells, since the transferrin receptor (TfR) is overexpressed in a broad range of cancers (Cazzola et al., Blood. 1990; 75(10):1903-19; Reizenstein, Med Oncol Tumor Pharmacother. 1991; 8(4):229-33). Specific targeting of drugs to cancer cells with Tf may help alleviate nonspecific toxicity associated with chemotherapy and radiation treatments (Saul et al., J Control Release. 2006; 114(3):277-87; Kreitman, Aaps J. 2006; 8(3): E532-51). Tf conjugates of cytotoxins including methotrexate (MTX), artemisinin, and diphtheria toxin (DT) have been reported, as well as Tf conjugates with novel payloads such as liposomally encapsulated drugs and siRNA (Lim and Shen, Pharm Res. 2004; 21(11): 1985-92; Lai et al., Life Sci. 2005; 76(11): 1267-79; Johnson et al., J Biol Chem. 1988; 263(3): 1295-300; Hu-Lieskovan et al., Cancer Res. 2005; 65(19): 8984-92; Tros et al., J Drug Target. 2006; 14(8):527-35; Maruyama et al., J Control Release. 2004; 98(2):195-207; Chin et al., J Control Release. 2006; 112(2):199-207).

Several chemotherapeutic agents may be bound to transferrin via available lysine residues using a glutaraldehyde reaction to form a chemical linking group. The glutaraldehyde can be used to activate the chemotherapeutic agent either when the agent and transferrin are in solution together or the chemotherapeutic agent can be activated and then mixed in solution with the transferrin. Paclitaxel has been bound via glutaraldehyde reaction to Transferrin; see, for example, U.S. Pat. Nos. 6,825,166; and 7,417,023; and U.S. Patent Application No. 20090181048. However, such glutaraldehyde linkages can inhibit or prevent release of the chemotherapeutic upon cellular uptake.

SUMMARY OF THE INVENTION

Described herein are novel compositions comprising a protein, such as albumin or transferrin, and a taxane or taxoid which does not utilize a linking group between the taxane and protein. The compositions, despite the lack of a linking group between the taxane and protein, are chromatographically stable. Such compositions have shown orders of magnitude of greater activity in inhibition of cellular proliferation, for example, with respect to glutaraldehyde-linked taxane-transferrin conjugates. Further, such compositions can be substantially free of non-ionic surfactants, such as Cremophor EL, and are useful in the treatment of cancers, such as breast cancer.

In one aspect, the present disclosure provides methods for preparing a composition, comprising combining (A) a first aqueous solution comprising a protein; and (B) a second solution comprising (i) a taxane or taxoid; (ii) a non-ionic surfactant; and (iii) an alcohol, to provide a third aqueous solution; adjusting the pH of the third aqueous solution to between about 7.9 and about 8.3; and purifying the pH-adjusted third aqueous solution to remove solutes having a molecular weight less than 10,000 Da.

In another aspect, the present disclosure provides compositions prepared according to the preceding aspect.

In another aspect, the present disclosure provides compositions comprising (i) a protein; (ii) a taxane or taxoid; and (iii) a pharmaceutically acceptable diluent, wherein the taxane or taxoid either (a) is bonded with the protein via a direct bond between the taxane or taxoid and the protein; or (b) forms a complex with the protein.

In another aspect, the present disclosure provides methods for treating a cancer in a patient in need of such treatment comprising providing to the patient a therapeutically effective amount of a composition according to or prepared according to the preceding aspects of the disclosure.

DETAILED DESCRIPTION OF THE INVENTION

Figure 1:
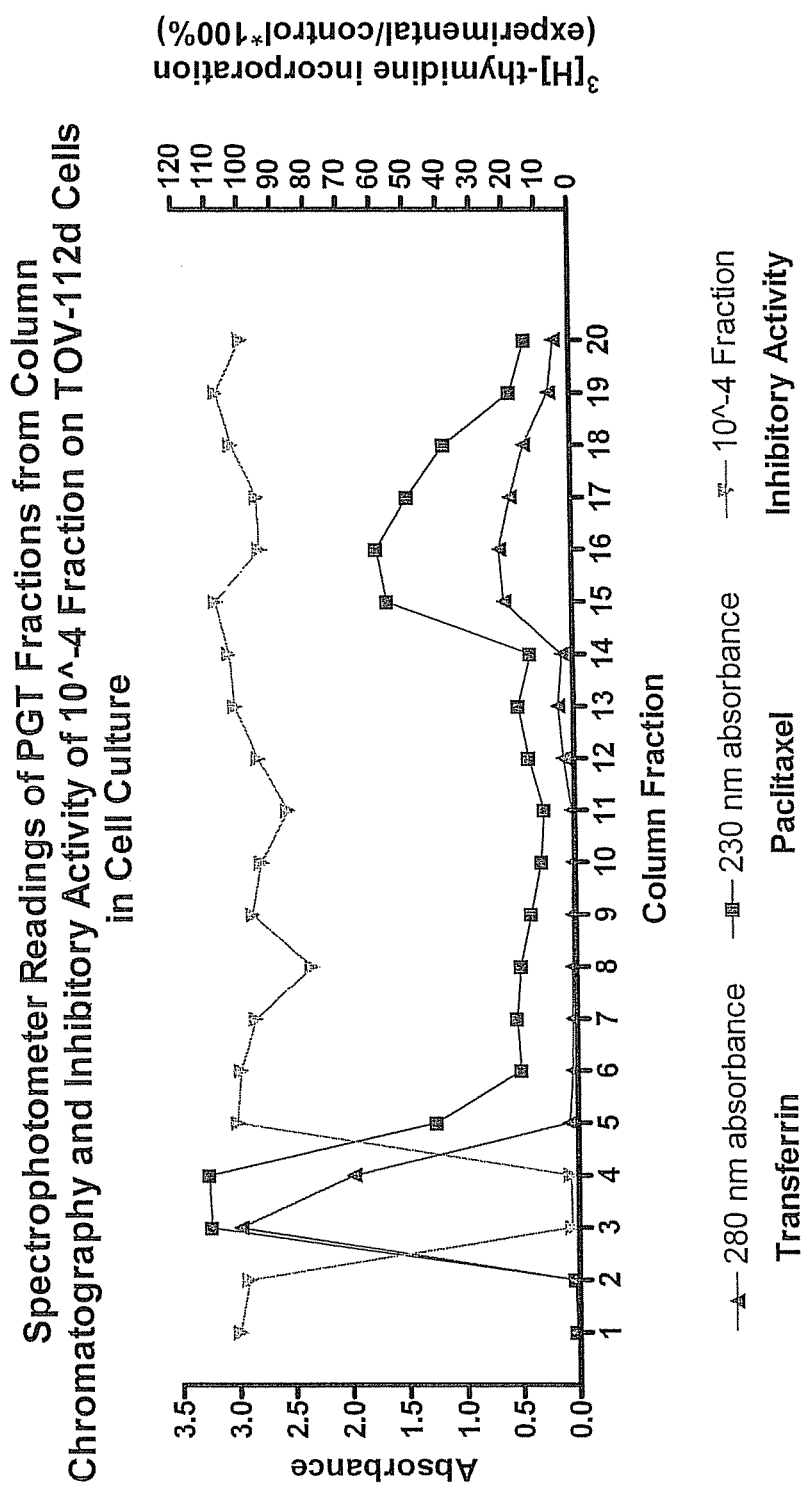
FIG. 1 is a graph of spectrophotometer readings for PGT fractions from column chromatography and inhibitory activity of 1:10,000 dilutions of fractions to TOV-112d cells in cell culture.
Figure 2:
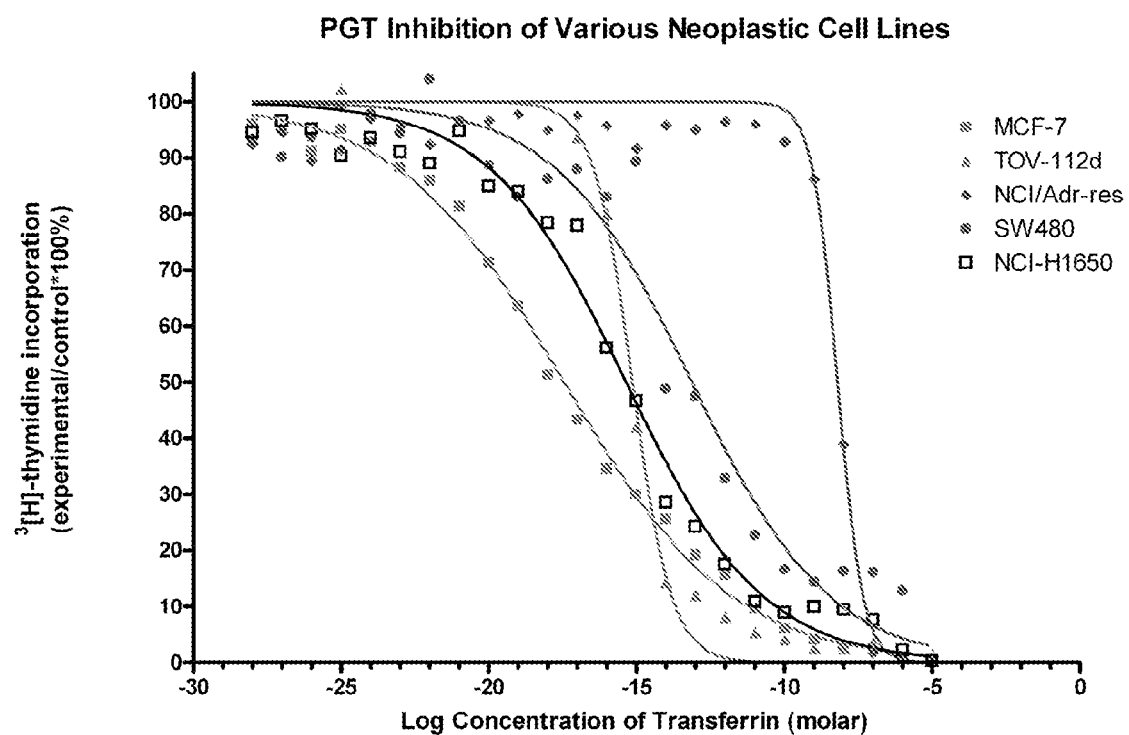
FIG. 2 is a graph of inhibition of MCF-7, TOV-112D, NCI/Adr-Res, SW480, and NCI-H1650 cells by PGT of Example 1 in cell culture.

In a first aspect, compositions of the invention can be prepared by, first, combining (A) a first aqueous solution comprising a protein, such as albumin or metal-transferrin; and (B) a second solution comprising (i) a taxane or taxoid; (ii) a non-ionic surfactant; and (iii) an alcohol, to provide a third aqueous solution.

The first aqueous solution is generally an aqueous solution and contains the protein at a concentration between about $8.5 \times 10^{-5}$ M and $8.5 \times 10^{-4}$ M; or between about $1.5 \times 10^{-4}$ M and $5.5 \times 10^{-4}$ M. The second solution can contain the taxane or taxoid at a concentration between about $9.0 \times 10^{-4}$ M and $9.0 \times 10^{-3}$ M; or between about $2.0 \times 10^{-3}$ M and $6.0 \times 10^{-3}$ M; and the non-ionic surfactant at a concentration between about 25 v/v % and 75 v/v % or between about 40 v/v % and 60 v/v %.

The first and second solutions can be combined by adding the second solution to the first solution, in certain embodiments, by dropwise addition. The temperature of the solutions can be maintained at a temperature between about 27° C. and 35° C.; or about 29° C. and 33° C. while the solutions are being combined.

The term "protein" as used herein refers to organic compounds made of amino acids arranged in a linear chain and, preferably, folded into a globular or fibrous form (i.e., a stable conformation). The amino acids in a protein are joined together by the peptide bonds between the carboxyl and amino groups of adjacent amino acid residues. The sequence of amino acids in a protein can be defined, for example, by the sequence of a gene. In general, the genetic code specifies 20 standard amino acids; however, proteins may contain other amino acids such as selenocysteine and pyrrolysine. The residues in a protein may be chemically modified by post-translational modification, which can alter the physical and chemical properties, folding, stability, activity, and ultimately, the function of a protein. In certain embodiments, a protein herein has at least 30 amino acid residues.

Suitable proteins for use in the present disclosure include, but are not limited to albumin, transferrin, metal-transferrin, prolactin, or an epidermal growth factor, such as heparin-binding EGF-like growth factor (HB-EGF), transforming growth factor-α (TGF-α), amphiregulin (AR), epiregulin (EPR), epigen, betacellulin (BTC), neuregulin-1 (NRG1), neuregulin-2 (NRG2), neuregulin-3 (NRG3), and neuregulin-4 (NRG4). In certain embodiments, the protein is albumin, transferrin, or metal-transferrin. In other embodiments, the protein is albumin. In yet other embodiments, the protein is transferrin or metal-transferrin. In yet other embodiments, the protein is transferrin. In yet other embodiments, the protein is metal-transferrin. In other embodiments, the protein is an epidermal growth factor. In yet other embodiments, the protein is prolactin.

As used herein, "albumin" refers to polypeptides of the albumin family of proteins such as, but not limited to, human serum albumin, bovine serum albumin, ovalbumin, conalbumin, lactalbumin, parvalbumin; and including variants and derivatives thereof, such as genetically engineered or chemically modified albumin variants. The albumin utilized herein may be from any available source familiar to those skilled in the art, including, but not limited to, plasma-derived albumins and recombinant albumins, such as recombinant human serum albumin (e.g., CellPrime rAlbumin AF-G (Millipore Corporation, Billerica, Mass.) or Albumin-DX (InVitria, Fort Colins, Colo.)).

As used herein, "metal-transferrin" means transferrin having a metal capable of binding to the metal binding sites therein. Transferrin is a glycoprotein (molecular weight of about 80 kDa) that tightly and reversibly binds iron and contains two high-affinity Fe(III) binding sites, including, but not limited to, human transferrin, bovine transferrin, serotransferrin, lactotransferrin, ovotransferrin, and melanotransferrin; and including variants and derivatives thereof, such as genetically engineered or chemically modified transferrin variants. The transferrin utilized herein may be from any available source familiar to those skilled in the art, such as, but not limited to, plasma-derived transferrin and recombinant transferrins, such as recombinant human transferrin (e.g., CellPrime rTransferrin AF and CellPrime rTransferrin AF-S (Millipore Corporation, Billerica, Mass.); Optiferrin™ (InVitria, Fort Colins, Colo.)).

Metal-transferrins can be prepared by contacting apo-transferrin with a metal salt or coordination complex comprising the metal ion capable of binding to the metal binding sites in transferrin. Examples of metals capable of binding to the metal binding sites in transferrin include, but are not limited to, iron, gallium, indium, manganese, and platinum. Suitable metal salts or coordination complexes include, but are not limited to, Fe(II), Fe(III), Ga(III), In(III), Mn(II), Mn(III), and Pt(II) salts or coordination complexes, such as, but not limited to, cisplatin (cis-diamminedichloroplatinum (II)), $PtCl_2$, platinum (II) acetate, platinum (II) acetylacetonate ($Pt(acac)_2$), $FeCl_3$, $FeBr_3$, $Fe(NO_3)_3$, $Fe_2(SO_4)_3$, $MnCl_2$, $MnBr_2$, $MnCO_3$, $MnSO_4$, $GaCl_3$, $GaBr_3$, $GaI_3$, $Ga(NO_3)_3$, $Ga(ClO_4)_3$, $Ga_2(SO_4)_3$, $InCl_3$, $InBr_3$, $InI_3$, $In(NO_3)_3$, $In(ClO_4)_3$, and $In_2(SO_4)_3$. In one embodiment, the metal-transferrin is gallium-transferrin, and the metal salt or coordination complex is gallium nitrate. In one embodiment, the metal-transferrin is platinum-transferrin, and the metal salt or coordination complex is cisplatin. In one embodiment, the metal-transferrin is iron-transferrin, and the metal salt or coordination complex is $FeCl_3$.

The term "taxane or taxoid" as used herein, means diterpene-containing compounds produced by the plants of the genus *Taxus* (e.g., yews, such as, but not limited to, *Taxus baccata*, *Taxus brevifolia*, *Taxus canadensis*, *Taxus chinensis*, *Taxus cuspidata*, *Taxus floridana*, *Taxus globosa*, *Taxus sumatrana*, *Taxus wallichiana*), and synthetic and semi-synthetic forms thereof. Taxanes or taxoids include, for example, paclitaxel and docetaxel. Generally, such compounds may block cell growth by stopping mitosis by interfering with microtubules. The term "diterpene," as used herein, means chemical compounds having a carbon skeleton derived from four isoprene units (i.e., a $C_{20}$ carbon skeleton). Examples of diterpenes include, but are not limited to, taxadiene,

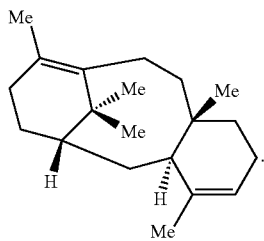

In one embodiment, the taxol is paclitaxel, docetaxel, or mixtures thereof. In another embodiment, the taxol is paclitaxel. In another embodiment, the taxol is docetaxel.

The term "non-ionic surfactant" as used herein means a substance which lowers the surface tension of the medium in which it is dissolved, and/or the interfacial tension with other phases, and, accordingly, is positively adsorbed at the liquid/vapor and/or at other interfaces. Examples of non-ionic surfactants include, but are not limited to, ethoxylated alkyl poly(ethylene oxide)s, alkylphenol poly(ethylene oxide)s, copolymers of poly(ethylene oxide) and polypropylene oxide) (e.g., poloxamers, such as BASF PLURONIC® products), alkyl polyglucosides (e.g., octyl glucoside or decyl maltoside), fatty alcohols (e.g., cetyl alcohol, oleyl alcohol), and polysorbates. Further examples of non-ionic surfactants include, but are not limited to, 8-methyl-1-nonanol propoxylate-block-ethoxylate, ALKANOL® 6112, allyl alcohol 1,2-butoxylate-block-ethoxylate, Brij® 30, Brij® 52, Brij® 72, Brij® 78, Brij® 92V, Brij® 93, Brij® 97, Brij® 98, Brij® 010, Brij® 5100, Brij® 510, Brij® 58, IGEPAL® CA-210, IGEPAL® CA-520, IGEPAL® CA-720, IGEPAL® CO-210, IGEPAL® CO-520, IGEPAL® CO-630, IGEPAL® CO-720, IGEPAL® CO-890, IGEPAL® DM-970, MERPOL® A, MERPOL® DA, MERPOL® HCS, MERPOL® OJ, MERPOL® SE, MERPOL® SH, polyethylene-block-poly(ethylene glycol), polyoxyethylene tridecyl ether, polyoxyethylene sorbitan tetraoleate, polyoxyethylene sorbitol hexaoleate, sorbitan monopalmitate, TWEEN® 20, TWEEN® 40, TWEEN® 60, TWEEN® 85, Tergitol® NP-9, Triton® N-101, Triton® SP-135, Triton® X-100, Triton® X-114, Triton® X-405, Triton® X-100, Zonyl® FS-300, Zonyl® FSA, Zonyl® FSE, Zonyl® FSJ, Zonyl® FSK, Zonyl® FSN, Zonyl® FSN-100, Zonyl® FSO, Zonyl® FSO-100, Cremophor® A25, Cremophor® A6, and Cremophor® EL. In one embodiment, the non-ionic surfactant comprises ethoxylated castor oil, such as Cremophor® EL.

The term "alcohol" as used herein, means a compound of the formula, $R(-OH)_n$, where R is a $C_{1-10}$ alkyl group, and n is 1, 2, or 3. When n is 1, examples of alcohols include, but are not limited to, methanol, ethanol, butanol, propanol, hexanol, octanol, and decanol. When n is 2, examples of alcohols include, but are not limited to, ethylene glycol and propylene glycol. When n is 3, examples of alcohols include, but are not limited to, glycerol. The term "alkyl" as used herein, means a straight or branched chain saturated hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. In certain embodiments, the alcohol is methanol, ethanol, isopropanol, or n-propanol. In another embodiment, the alcohol is methanol or ethanol. In another embodiment, the alcohol is ethanol.

Next, the pH of the third aqueous solution is adjusted to between about 7.9 and about 8.3. Such can be accomplished by adding a base. In one embodiment, the base is a hydroxide base. Examples of suitable hydroxide bases include, but are not limited to, sodium hydroxide, potassium hydroxide, lithium hydroxide, rubidium hydroxide, cesium hydroxide, calcium hydroxide, strontium hydroxide, barium hydroxide, or mixtures thereof. In another embodiment, the hydroxide base is sodium hydroxide. The temperature of the third aqueous solution can be maintained at a temperature between about 27° C. and 35° C.; or about 29° C. and 33° C. while the pH is being adjusted.

Finally, the pH-adjusted third aqueous solution is purified to remove solutes having a molecular weight less than 10,000 Da. Such purification can be according to any methods familiar to one skilled in the art. For example, in one embodiment, the pH-adjusted third solution is purified by dialysis against a buffer solution using a dialysis membrane having a molecular weight cutoff of 10,000 Da. The buffer solution can comprise any buffer suitable for administration to a patient, such as, but not limited to, sterile physiological balanced salt solutions having a physiological pH and salt concentration. Such solutions can include ions such as sodium, potassium, calcium, magnesium, and chloride, and additional components such as glucose. Examples of physiological balanced salt solutions include, Alsever's solution, Earle's balanced salt solution (EBSS), Gey's balanced salt solution (GBSS), Hank's balanced salt solution (HBSS), (Dulbecco's) Phosphate buffered saline (PBS), Puck's balanced salt solution, Ringer's balanced salt solution (RBSS), Simm's balanced salt solution (SBSS), TRIS-buffered saline (TBS), and Tyrode's balanced salt solution (TBSS). In one embodiment, the buffer solution is Hank's Balanced Salt Solution. The dialysis can be repeated multiple times. In one embodiment, the dialysis is repeated at least two times by replacing the external dialysis solution with fresh solution.

Optionally, the purified pH-adjusted third solution can be filter sterilized to provide a filter-sterilized composition of the invention. In one embodiment, the solution can be passed through a filter having an average pore diameter of about 0.2 microns to about 0.5 microns. For example, the solution can be sterilized by passing through a 0.45 micron filter. In another example, the solution can be sterilized by passing through a 0.22 micron filter.

Further, and optionally, the pH-adjusted third aqueous solution, the purified pH-adjusted third solution, or the sterilized composition can be further purified by size-exclusion chromatography according to methods known to one skilled in the art. For example, the solution or composition can be further purified via column chromatography using an appropriate size exclusion chromatography phase, such as a Sephadex (a crosslinked dextran gel, e.g., G-10 Sephadex), and using a pharmaceutically acceptable diluent as eluant for the column. The eluant can be any of the sterile physiological balanced salt solutions noted above. In one example, the eluant is PBS. As necessary, any solution eluted from the column can be filter sterilized as described above.

In certain embodiments, a first aqueous solution comprises albumin; and a second solution comprises paclitaxel; a non-ionic surfactant; and an alcohol. In certain other embodiments, a first aqueous solution comprises albumin; and a second solution comprises paclitaxel; a non-ionic surfactant; and ethanol. In certain other embodiments, a first aqueous solution comprises albumin; and a second solution comprises paclitaxel; Cremophor® EL; and ethanol.

In certain embodiments, a first aqueous solution comprises a metal-transferrin; and a second solution comprises paclitaxel; a non-ionic surfactant; and an alcohol. In certain other embodiments, a first aqueous solution comprises a metal-transferrin; and a second solution comprises paclitaxel; a non-ionic surfactant; and ethanol. In certain other embodiments, a first aqueous solution comprises a metal-transferrin; and a second solution comprises paclitaxel; Cremophor® EL; and ethanol. In certain other embodiments, a first aqueous solution comprises a gallium-transferrin; and a second solution comprises paclitaxel; Cremophor® EL; and ethanol.

Another aspect provides a composition prepared according to the preceding methods and any embodiment thereof. Without being bound by any one theory of structure or operation, the preceding composition can comprise or consist essentially of a protein, such as albumin or metal-transferrin, a taxane or taxoid, and a pharmaceutically acceptable diluent, wherein the taxane or taxoid is either (i) bonded with the protein, such as albumin or metal-transferrin via a direct bond between the taxane or taxoid and the protein; or (ii) forms a complex with the protein.

As used herein, a "complex" means a molecular entity formed by the assembly of component molecules into an aggregate. Examples of aggregates include, but are not limited to, aggregates (1) of oppositely charged free ions or ion pairs; (2) of molecules held together by electrostatic attraction; and (3) where one molecule or a plurality of molecules forms a cavity in which another molecule is located; generally, there is no covalent bonding between the molecules, the attraction being generally due to van der Waals forces. A micelle is an example of such a complex. In one embodiment, a taxane or taxoid is bonded with a protein, such as albumin or metal-transferrin, via a direct bond between the taxane or taxoid and the protein. In another embodiment, the taxane or taxoid forms a complex with the protein.

In one embodiment, the protein comprises albumin or metal-transferrin. In another embodiment, the protein comprises albumin. In another embodiment, the protein comprises metal-transferrin. In certain embodiments where the protein comprises metal-transferrin, the metal-transferrin is gallium-transferrin, iron-transferrin, indium-transferrin, zinc-transferrin, manganese-transferrin, platinum-transferrin, or a mixture thereof. In one particular embodiment, metal-transferrin is gallium-transferrin.

In any of the preceding embodiments, the taxane or taxoid is paclitaxel or docetaxel. In another embodiment, the taxane or taxoid is paclitaxel. In another embodiment, the taxane or taxoid is docetaxel.

In any of the preceding embodiments, the taxane or taxoid is bonded with the albumin or metal-transferrin via a direct bond between the taxane or taxoid.

In any of the preceding embodiments, the taxane or taxoid forms a complex with the albumin or metal-transferrin.

In any of the preceding embodiments, the taxane or taxoid is in a micelle with the albumin or metal-transferrin.

Methods of Use

In another aspect, the present disclosure provides methods for treating a cancer in a patient in need of such treatment comprising providing to the patient a therapeutically effective amount of a composition prepared or as described above.

In one embodiment, the cancer being treated is a sarcoma, a lymphoma, a leukemia, a melanoma, a multiple myeloma, pancreatic cancer, esophageal cancer, bladder cancer, testicular cancer, thyroid cancer, brain cancer, gynecologic cancers, pediatric solid tumors, colorectal cancer, prostate cancer, liver cancer, renal cancer, gastric cancer, head and neck cancers, breast cancer, ovarian cancer, colon cancer, or lung cancer. In another embodiment, the cancer being treated is breast cancer, ovarian cancer, colon cancer, or lung cancer. In another embodiment, the cancer being treated is breast cancer. In another embodiment, the cancer being treated is ovarian cancer. In another embodiment, the cancer being treated is colon cancer. In another embodiment, the cancer being treated is lung cancer.

As used here, the terms "treatment" and "treating" means (i) preventing the disease; for example, preventing a disease, condition or disorder in an individual who may be predisposed to the disease, condition or disorder but does not yet experience or display the pathology or symptomatology of the disease; (ii) inhibiting the disease; for example, inhibiting a disease, condition or disorder in an individual who is experiencing or displaying the pathology or symptomatology of the disease, condition or disorder; (iii) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (iv) eliciting the referenced biological effect.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used here, a subject "in need thereof" refers to a subject that has the disorder or disease to be treated or is predisposed to developing the disease or disorder.

EXAMPLES

Example 1

Preparation of Paclitaxel-Gallium-Transferrin (PGT) Composition

Gallium-transferrin (Ga-tf) was prepared for use in preparation of Paclitaxel-Gallium-Transferrin (PGT). Ga-tf was made by dissolving 500 mg of human transferrin (Sigma Aldrich; St. Louis, Mo.) in 9.0 mL of acetic acid buffer (20 mM acetic acid containing 150 mM NaCl, pH 3.5). To the transferrin containing solution was added 1.0 mL of a solution containing 38.6 mg of gallium nitrate in 5.0 mL of acetic acid buffer. The pH was slowly raised to 7.4 using 1 M NaHCO$_3$. The final solution was incubated for two days at 4° C. After incubation the solution was dialyzed (m.w. cutoff of 10,000) against 500 mL of Hanks Balanced Saline Solution (HBSS) overnight, two times. The mixture was filter sterilized (0.45 micron filter) and stored at 4° C.

The following steps were used to combine paclitaxel to Ga-tf. The temperature of all compounds was kept at 31° C. throughout the reaction. First, 4 mL of Cremaphor EL (Sigma Aldrich; St. Louis, Mo.) was put in a glass centrifuge tube. Then, 25 mg of Paclitaxel from *Taxus yannanensis* (Sigma-Aldrich; St. Louis, Mo.) was added to the Cremaphor EL. Four milliliters of ethanol was used to wash the paclitaxel from the ampule. The centrifuge tube was placed on a stirring hot plate and the temperature kept at 31° C. In a separate centrifuge tube 1.75 mL of phosphate buffer and 2.25 mL of Ga-tf (from above) were mixed. The paclitaxel-alcohol-Cremaphor EL mixture was then added dropwise to the Ga-tf mixture while on the stirring plate. After the paclitaxel-alcohol-Cremaphor EL was added, NaOH was added dropwise to bring the pH of the mixture to between 7.9 and 8.3. The compound was stirred overnight then dialyzed (m.w. cutoff of 10,000) overnight in HBSS, two times. The final compound was filter sterilized (0.45 micron filter) and stored at 4° C.

Method for Column Chromatography:

Size Exclusion Chromatography was used to separate unattached paclitaxel from Paclitaxel-Gallium-Transferrin (PGT). The top of a 10 mL serological pipette was cut off and used as a column. A small ball of glass wool was pushed to the bottom of the column. The column was attached to a ring stand and washed with 20 mL of 0.1 M Phosphate Buffered Saline (PBS), pH 7.4. Five grams of dry G-10 Sephadex (molecular weight cutoff of 700) was added to 10 mL of PBS and allowed to swell overnight at room temperature. After swelling was complete, the fines were removed via aspiration. Then, 2.25 mL of PBS was added to the swelled Sephadex to make a 75% slurry. The slurry was added to the column and allowed to pack by gravity. The column was washed with 20 mL of PBS. One mL of PGT was added to the column and fraction collection was initiated. PBS was continually added to the column and twenty 1 mL fractions were collected. Spectra analysis of the size-exclusion chromatography fractions was done on a Beckman DU-6 UV-Visible Spectrophotometer. Light absorption at 230 nm for paclitaxel and 280 nm for transferrin protein was done for each fraction. Results of the chromatographic separation are shown in FIG. 1.

of the untreated control. The experiments were repeated a minimum of three times independently.

Table 1 illustrates the inhibition of MCF-7 cells using various metal-transferrins conjugated to a taxane via a glutaraldehyde reaction. In contrast, Table 2 provides inhibition of various cancer cell lines using the PGT composition as described above In particular, it can be noted that for MCF-7 breast cancer cells, the PGT composition of the taxane or taxoid displays an $IC_{50}$ of $4.5 \times 10^{-13}$ M while paclitaxel conjugated to gallium-transferrin (Ga-tf) via a gutaraldehyde reaction has an $IC_{50}$ of $3.8 \times 10^{-11}$ M.

TABLE 1

Inhibition of MCF-7 Cells by Transferrin Based Chemotherapeutic Agents

| Metal - Transferrin | $IC_{50}$ of Drugs bound by a Glutaraldehyde Reaction to the Surface of Transferrin (M) | | | |
| --- | --- | --- | --- | --- |
| | No Drug | Daunorubicin | Doxorubicin | Paclitaxel |
| Fe-tf | — | $2.2 \times 10^{-7}$ | $6.8 \times 10^{-9}$ | $5.4 \times 10^{-11}$ |
| Ga-tf | $3.4 \times 10^{-6}$ | $3.6 \times 10^{-7}$ | $2.3 \times 10^{-10}$ | $3.8 \times 10^{-11}$ |
| In-tf | $2.7 \times 10^{-6}$ | $2.7 \times 10^{-8}$ | — | $2.0 \times 10^{-10}$ |

TABLE 2

PGT Inhibition of Cell Lines

| Cell Line | | Cells/Well | $IC_{50}$ | $IC_{90}$ |
| --- | --- | --- | --- | --- |
| MCF-7 | Breast Cancer | 3000 | $3.6 \times 10^{-18}$ (n = 16) | $5.8 \times 10^{-12}$ (n = 16) |
| TOV-112D | Ovarian Cancer | 3000 | $7.5 \times 10^{-16}$ (n = 5) | $2.1 \times 10^{-14}$ (n = 5) |
| NCI/Adr-Res | Ovarian Cancer | 3000 | $6.8 \times 10^{-9}$ (n = 3) | $5.1 \times 10^{-8}$ (n = 3) |
| SW480 | Colon Cancer | 1500 | $1.6 \times 10^{-13}$ (n = 5) | $9.9 \times 10^{-9}$ (n = 5) |
| NCI-H1650 | Lung Cancer | 3000 | $7.3 \times 10^{-16}$ (n = 3) | $2.5 \times 10^{-11}$ (n = 3) |

Example 2

Cytotoxicity of PGT in Cell Culture

Human cancer cell lines were obtained from the American Type Culture Collection (Rockville, Md.); the NCI/Adr-Res cell line came from the National Cancer Institute (Bethesda, Md.). The cancer cell lines were maintained in alpha-MEM supplemented with 10% fetal calf serum, 1 mM glutamine and 0.05 mg/mL gentamicin (Life Technologies, Inc., Frederick, Md.) in 5% $CO_2$ at 37° C. Cells were removed from cell culture flask or plate by trypsin-EDTA (0.05% trypsin and 0.53 mM EDTA) digestion.

Cell growth was measured with a $^3$[H]-thymidine incorporation assay. Cancer cells were plated into each well of a 96-well cell culture plate as noted in Table 2 (e.g., MCF-7 cells were plated at 3000 cells/well) and incubated overnight. Culture media was replaced with media containing increasing concentrations of transferrin based drugs, and the cells were incubated with these drugs for 3 days. Then, $^3$[H]-thymidine (0.1 uCi/well) was added to each well for the last 16 hours of incubation. The cells were removed from the plate by trypsin-EDTA digestion and harvested onto a glass-fiber filter (Skatron basic96 Harvester, Shatron Inc., Sterling, Va.). The radioactivity incorporated into the cellular DNA was determined by liquid scintillation counting (LS 6500, Beckman Co., Fullerton, Calif.). Cell proliferation was quantitated by $^3$[H]-thymidine incorporation and expressed as a percentage Example 3

Reversal with Iron Loaded Transferrin

Iron-loaded transferrin (Fe-tf) was prepared for competition experiments with PGT. Fe-tf was made by dissolving 500 mg of human transferrin (Sigma Aldrich; St. Louis, Mo.) in 9.0 mL of acetic acid buffer (20 mM acetic acid containing 150 mM NaCl, pH 3.5). To the transferrin containing solution was added 1.0 mL of a solution containing 30.0 mg of ferric chloride in 10.0 mL of acetic acid buffer. The pH was slowly raised to 7.4 using 1 M $NaHCO_3$. The final solution was incubated for two days at 4° C. After incubation the solution was dialyzed (m.w. cutoff of 10,000) against 500 mL of Hanks Balanced Saline Solution (HBSS) overnight, two times. The mixture was filter sterilized (0.45 micron filter) and stored at 4° C.

Human MCF-7 breast cancer cells were removed from a cell culture flask by trypsin-EDTA (0.05% trypsin and 0.53 mM EDTA) digestion. Cancer cells (MCF-7 cells at 3000 cells/well) were plated into each well of a 96-well cell culture plate and incubated overnight. Culture media was replaced with media containing increasing concentrations of PGT or PGT with Fe-tf added at 10 and 100 times the concentration of the PGT. The cells were incubated with these drugs for 3 days. Cell growth was measured with a $^3$[H]-thymidine incorporation assay. After $^3$[H]-thymidine (0.1 uCi/well) was added to each well for the last 16 hours of incubation, the cells were removed from the plate by trypsin-EDTA digestion and harvested onto a glass-fiber filter (Skatron basic96 Harvester, Shatron Inc., Sterling, Va.). The radioactivity incorporated into the cellular DNA was determined by liquid scintillation counting (LS 6500, Beckman Co., Fullerton, Calif.). Cell proliferation was quantitated by $^3$[H]-thymidine incorporation and expressed as a percentage of the untreated control. The experiments were repeated a minimum of three times independently.

TABLE 3

Competitive Inhibition of the Transferrin Receptor With Paclitaxel-Gallium-Transferrin (PGT) and Iron-Transferrin (Fe-Tf) in the breast cancer cell line MCF-7

|  | $IC_{50}$ |
|---|---|
| PGT | $7.20 \times 10^{-16}$ M |
| PGT and 10X FeTf | $2.07 \times 10^{-15}$ M |
| PGT and 100X FeTf | $5.88 \times 10^{-14}$ M |

Example 4

Paclitaxel-Albumin

A paclitaxel-albumin composition was prepared by first adding 4 mL Cremaphor EL to a 50 mL round bottom centrifuge tube and heating the tube to 31° C. in a water bath. 25 mg of paclitaxel were added to the Cremaphor EL centrifuge tube by washing the paclitaxel with 4 mL 95% ethanol using multiple washes with a 1 mL pipette. A stir bar (flea size) was added and the solution stirred at 31° C. until mixed (approximately 45-60 minutes). After the paclitaxel has dissolved in the Cremaphor EL, 3.66 mL of 0.01 M phosphate buffer at 7.4 pH, and 0.34 mL of albumin (85 mg of albumin in 25% solution) were mixed in another round bottom centrifuge tube and a stir bar (flea size) was added. The albumin mixture was heated to 31° C. The heated albumin mixture was added drop wise to the paclitaxel mixture, making sure that each addition goes into solution before adding the next drop. This was done over a period of at least one hour The paclitaxel-albumin was allowed to stir for about 10 minutes to ensure all is mixed (the solution will be a little cloudy). The paclitaxel-albumin was poured into a small beaker with a stir bar and the pH tested. Then, 0.5 M NaOH was added drop wise to bring the pH from 7.3 to between 7.9 and 8.3, the beaker covered with paraffin, and stirred overnight. The paclitaxel-albumin was pipetted into dialysis tubing with 10,000 m.w. cutoff, the dialysis tubing was placed into 500 mL of phosphate buffer, and stirred overnight in the refrigerator, yielding a paclitaxel-albumin solution that was clear without a precipitant. Dialysis was repeated twice in phosphate buffer, 24 hrs. each at 4° C. in the refrigerator. The dialysis tubing was gently untied with forceps, the paclitaxel-albumin solution pipetted into a syringe and filter sterilized to yield 24 mL of paclitaxel-albumin solution.

Example 5

Cytotoxicity of Paclitaxel-Albumin in Cell Culture

Figure 3:
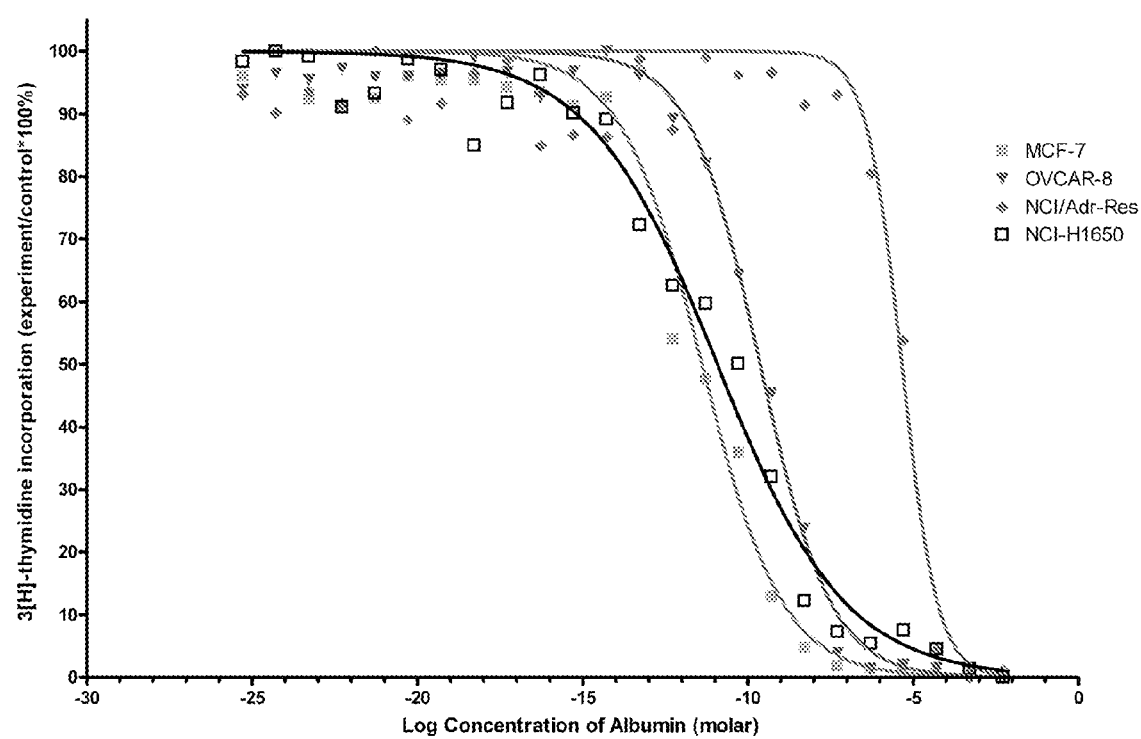
FIG. 3 is a graph of inhibition of MCF-7, OVCAR-8, NCI/Adr-Res, and NCI-H1650 cells by paclitaxel-albumin of Example 4 in cell culture.

The paclitaxel-albumin composition of Example 4 was tested for inhibition of cell lines according to the methods of Example 2. A summary of the results follow in Table 4 and are illustrated in FIG. 3.

TABLE 4

Paclitaxel-Albumin Inhibition of Cell Lines

| Cell Line | | Cells/Well | $IC_{50}$ | $IC_{90}$ |
|---|---|---|---|---|
| MCF-7 | Breast Cancer | 3000 | $4.0 \times 10^{-12}$ (n = 6) | $2.1 \times 10^{-09}$ (n = 6) |
| OVCAR-8 | Ovarian Cancer | 3000 | $3.1 \times 10^{-10}$ (n = 8) | $2.3 \times 10^{-08}$ (n = 8) |
| NCI/Adr-Res | Ovarian Cancer | 3000 | $4.5 \times 10^{-06}$ (n = 6) | $6.9 \times 10^{-05}$ (n = 6) |
| NCI-H1650 | Lung Cancer | 3000 | $1.2 \times 10^{-11}$ (n = 6) | $2.2 \times 10^{-07}$ (n = 6) |

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present invention includes any other applications in which embodiment of the above structures and fabrication methods are used. The scope of the embodiments of the present invention should be determined with reference to claims associated with these embodiments, along with the full scope of equivalents to which such claims are entitled.

We claim:

1. A composition comprising A) a complex consisting of (i) a metal-transferrin; and (ii) a taxane or taxoid that inhibits mitosis; and B) a pharmaceutically acceptable diluent,
   wherein the taxane or taxoid either (a) is bonded with the metal-transferrin via a direct bond between the taxane or taxoid and the metal-transferrin; or (b) forms a non-covalent complex with the metal-transferrin;
   the transferrin of the metal-transferrin is human transferrin, bovine transferrin, serotranferrin, lactotransferrin, ovotransferrin, or melanotransferrin, and
   the composition substantially lacks solutes having a molecular weight less than 10,000 Da.

2. The composition of claim 1, wherein the taxane or taxoid is paclitaxel or docetaxel.

3. The composition of claim 1, the metal-transferrin is gallium-transferrin, iron-transferrin, indium-transferrin, zinc-transferrin, manganese-transferrin, platinum-transferrin, or a mixture thereof.

4. The composition of claim 3, the metal-transferrin is gallium-transferrin.

5. The composition of claim 1, wherein the taxane or taxoid is paclitaxel.

6. The composition of claim 5, the metal-transferrin is gallium-transferrin.

7. The composition claim 1, wherein the taxane or taxoid is bonded with the metal-transferrin via a direct bond.

8. The composition of claim 1, wherein the taxane or taxoid forms a non-covalent complex with the metal-transferrin.

\* \* \* \* \*